(12) United States Patent
Spahn et al.

(10) Patent No.: US 9,301,866 B2
(45) Date of Patent: Apr. 5, 2016

(54) INFLATABLE FOOT CUSHION

(75) Inventors: James G. Spahn, Carmel, IN (US);
Brian D. Conway, Carmel, IN (US);
David P. Laughlin, Mooresville, IN
(US); Scott D. Rogers, Carmel, IN (US)

(73) Assignee: EHOB, INC., Indianapolis, IN (US)

( * ) Notice: Subject to any disclaimer, the term of this patent is extended or adjusted under 35 U.S.C. 154(b) by 32 days.

(21) Appl. No.: 13/432,068

(22) Filed: Mar. 28, 2012

(65) Prior Publication Data
US 2012/0253250 A1 Oct. 4, 2012

Related U.S. Application Data

(60) Provisional application No. 61/516,087, filed on Mar. 29, 2011.

(51) Int. Cl.
A61F 5/01 (2006.01)
A61F 5/058 (2006.01)

(52) U.S. Cl.
CPC ............ *A61F 5/012* (2013.01); *A61F 5/05816* (2013.01); *A61F 2005/0183* (2013.01); *A61H 2201/1697* (2013.01)

(58) Field of Classification Search
USPC .............. 602/12, 13, 27, 61, 63, 65; 128/882, 128/DIG. 23; 601/148, 151, DIG. 20; 606/201–204, 112
See application file for complete search history.

(56) References Cited

U.S. PATENT DOCUMENTS

| 4,198,961 | A | * | 4/1980 | Arkans | 601/152 |
|---|---|---|---|---|---|
| 4,266,298 | A | | 5/1981 | Graziano | |
| 5,328,445 | A | * | 7/1994 | Spahn et al. | 602/13 |
| 5,443,440 | A | * | 8/1995 | Tumey et al. | 601/152 |
| 5,489,259 | A | * | 2/1996 | Jacobs | A61F 5/012 128/882 |
| 6,007,559 | A | * | 12/1999 | Arkans | A61B 17/135 601/150 |
| 6,358,219 | B1 | * | 3/2002 | Arkans | 601/152 |
| 6,368,357 | B1 | * | 4/2002 | Schon et al. | 623/37 |
| 6,375,633 | B1 | * | 4/2002 | Endress | A61F 5/0111 128/882 |
| 7,044,924 | B1 | * | 5/2006 | Roth et al. | 601/151 |
| 7,871,387 | B2 | * | 1/2011 | Tordella | A61F 5/34 128/DIG. 20 |
| 7,909,787 | B2 | * | 3/2011 | Ravikumar | 602/13 |
| 8,216,165 | B2 | * | 7/2012 | Ravikumar et al. | 602/13 |
| 8,313,450 | B2 | * | 11/2012 | Ben-Nun | 602/23 |
| 2003/0191420 | A1 | | 10/2003 | Kuiper et al. | |
| 2008/0294079 | A1 | | 11/2008 | Sterling et al. | |
| 2011/0009784 | A1 | * | 1/2011 | Li et al. | 601/151 |

FOREIGN PATENT DOCUMENTS

WO    WO 99/11204    3/1999

OTHER PUBLICATIONS

Canadian Patent Application No. 2772758 Examination Report mailing date Aug. 7, 2014.

* cited by examiner

*Primary Examiner* — Ophelia A Hawthorne
(74) *Attorney, Agent, or Firm* — Taft Stettinius & Hollister LLP

(57) ABSTRACT

An inflatable foot cushion to reduce the force amplifications upon the heel of a foot received therein when the body is in a supine position.

17 Claims, 8 Drawing Sheets

INFLATABLE FOOT CUSHION

CROSS-REFERENCE TO RELATED APPLICATIONS

The present application claims priority to U.S. Provisional Patent Application 61/516,087, filed Mar. 29, 2011.

BACKGROUND OF THE INVENTION

The present invention relates generally to the field of inflatable devices for supporting the human body, and more particularly is concerned with a novel improved inflatable foot cushion to counter the force amplifications experienced by the foot, and particularly the heel area of the foot, when the body is in the supine position.

In the supine position, the foot assumes the shape of a wedge that tapers from the toes down to the heel. The mechanical force amplifications that are typically associated with a wedge are therefore also experienced by the wedge-shaped foot. The heel area, and more specifically the points of contact between the heel area and the substrate upon which the body is lying in the supine position, experiences mechanical force amplifications that are analogous to those experienced by the working edge of the typical wedge. In addition, when in the supine position, the lower legs function as levers with the heel areas serving as fulcrums, further amplifying the mechanical forces acting upon the heel areas.

The recognition that heel ulcers are caused by such mechanical forces (pressure, shear and frictional stresses) on the heel became clinically significant in the early 1980's. Since that time it has been found that offloading mechanical forces on the heel is the ideal way to prevent a pressure ulcer of the heel from developing (see NPUAP and EPUAP Guidelines). During the era of using pillows to offload mechanical forces on the heel, the occurrence of pressure ulcers of the heel continued to increase. Pressure ulcers of the heel are now running a close second to sacral pressure ulcers. When considering the deep tissue injury component of the pressure ulcer, pressure ulcers of the heel are now first in occurrence (see Vangilder, MacFarlane, Harrison, Lachenbruch and Meyer 254-261).

In 1994, a three-chambered Inflatable Foot Cushion was patented (U.S. Pat. No. 5,328,445). The prevention and treatment of pressure ulcers of the heel and other types of foot wounds have been exceptional when this patented inflatable foot cushion has been in use. The foot resting chamber of that device was constructed to resemble the keel of a boat. The objectives of the two main inflatable chambers of the patented Inflatable Foot Cushion that defined the foot resting chamber were the offloading the mechanical forces on the heel; the giving of symmetrical static air support to the calf, ankle and foot; and (3) the supporting of the sole of the foot to prevent foot drop and resultant injury. The third main chamber of that patented Inflatable Foot Cushion was an independent chamber (16) that was used beneath the two main chambers as an accessory chamber to elevate the inflatable foot cushion.

SUMMARY OF THE INVENTION

The present invention is a novel improved inflatable foot cushion that addresses and resolves issues that arose in the prevention of ulcers of the heel when using the three-chambered Inflatable Foot Cushion of U.S. Pat. No. 5,328,445, which is incorporated by reference herein.

One embodiment of the improved inflatable foot cushion of the present invention is an inflatable foot cushion to reduce the force amplifications upon the heel of a foot received therein when the body is in a supine position, comprising: an inflatable main chamber having two inflatable downwardly-sloping sides and a two-sided inflatable foot chamber with each side of the inflatable foot chamber being connected in fluid communication with one of the two downwardly-sloping sides that support with static air pressures the calf, ankle and foot of a body in a supine position, leaving the heel of the foot free of support, when they are positioned within the inflatable main chamber; a plurality of inflatable, adjustable calf straps connected in fluid communication at one end thereof with one of the downwardly-sloping sides and removably and adjustably affixed at the other end thereof to the other downwardly-sloping side that overlay the skin on a calf along the tibia when a calf is positioned within the inflatable main chamber; an inflatable, adjustable foot strap connected in fluid communication at one end thereof with one side of the inflatable foot chamber and removably and adjustably affixed at the other end thereof to the other side of the inflatable foot chamber that overlays the skin on the top of a foot when a foot is positioned within the inflatable main chamber; and an inflatable, adjustable two-sided foot sole cushion with one side of each side connected in fluid communication to one side of the inflatable foot chamber and with the other side of each side removably and adjustably affixed to each other, whereby the two-sided foot sole cushion overlays and adjusts to the contour of the sole of a foot positioned within the inflatable foot chamber.

DESCRIPTION OF THE PREFERRED EMBODIMENT

Figure 2:
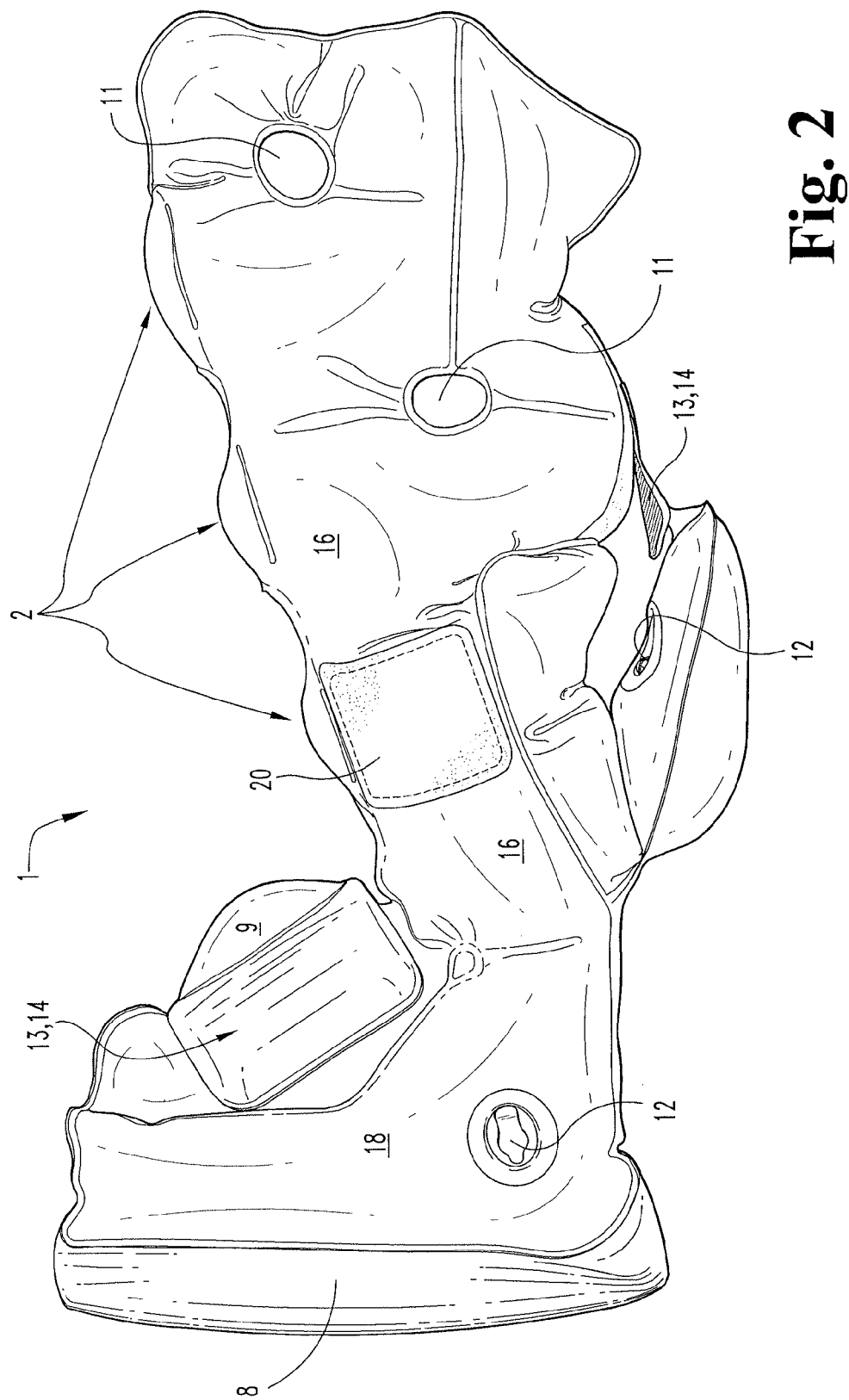
FIG. 2 is a left side elevation view of the novel inflatable foot cushion of the present invention.
Figure 8:
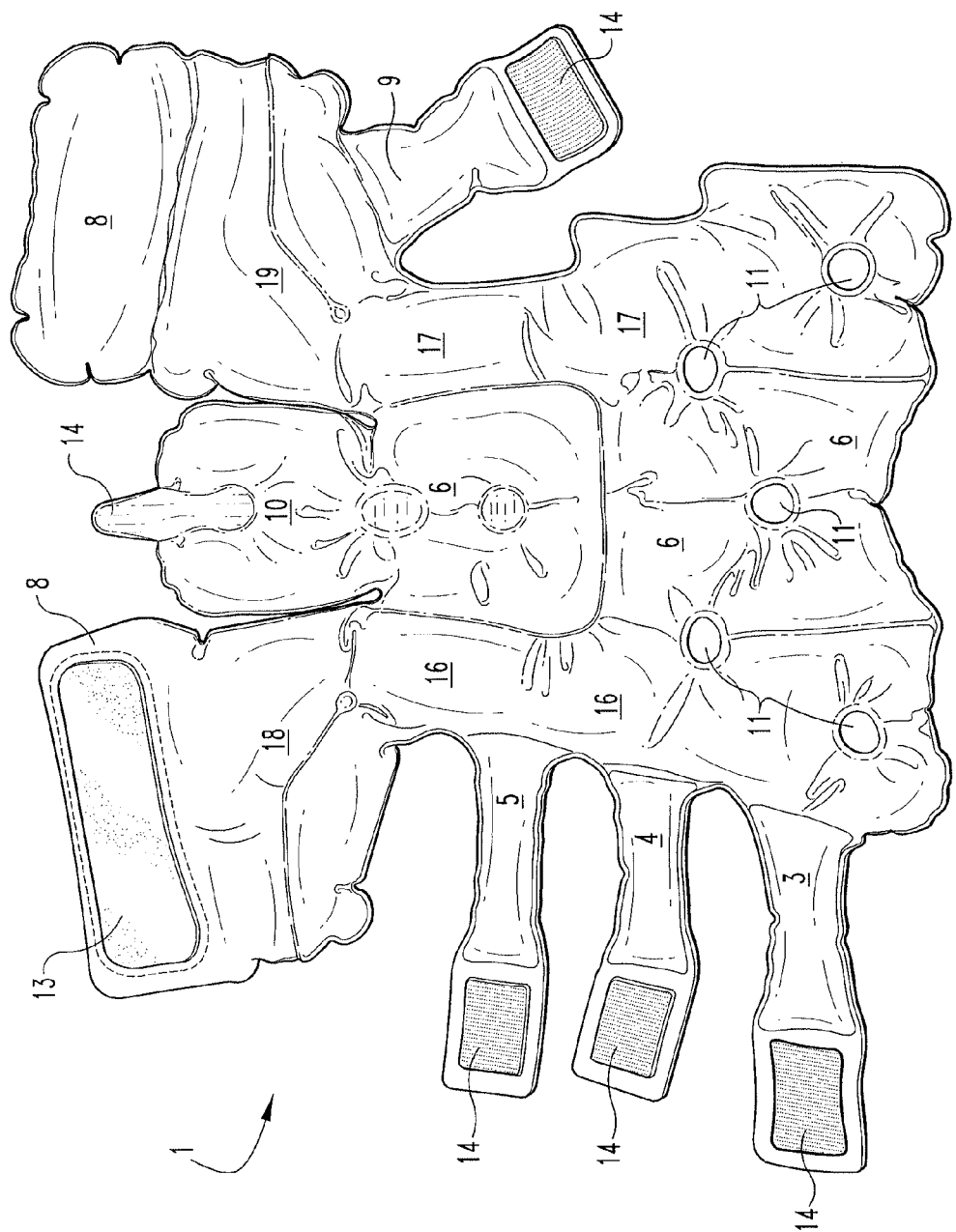
FIG. 8 is an exploded top plan view of the inflated novel inflatable foot cushion of the present invention showing the relationships of its constituent parts.

Referring now to FIG. 8, which is an exploded top plan view of an inflated novel inflatable foot cushion (1) of the present invention, and which illustrates the relationships of its novel constituent parts, and which also illustrates how two pliable plastic sheets have been joined together by conventional means to form the novel inflatable chambers and straps of the inflatable foot cushion (1) of the present invention. Referring to FIG. 2, there is one inflation port (12) for all of the air inflatable chambers shown in FIG. 8, all of which are in fluid communication with each other, with one exception. FIG. 2 also illustrates an inflation port (12) for independent air inflatable chamber (10), which is not in fluid communication with the other chambers illustrated in FIG. 8, and which is of the same size and has the same functionality as does independent air inflatable cushion 16 of the Inflatable Foot Cushion of U.S. Pat. No. 5,328,445. The only difference between present independent inflatable chamber 10 and the inflatable cushion (16) of U.S. Pat. No. 5,328,445 is that the present invention's cushion (10) is kept in it adjustable positions by hook and loop fasteners (13, 14). Independent inflatable chamber 10 is not a part of the presently claimed invention.

The first novel improvement of the improved inflatable foot cushion (1) of the present invention is the addition of air-inflated, adjustable calf straps (2) that secure the novel inflatable foot cushion (1) to the calf, ankle and foot ("CAF") of a patient, which air inflated calf straps effectively protect a patient's skin of the calf over the tibia when the calf is secured within the novel inflatable foot cushion (1) by the inflated adjustable calf straps (2). This is accomplished by filling the individual inflatable calf straps (3, 4, 5) with static air, each strap being formed, as are all other static air chambers of the novel inflatable foot cushion (1) of the present invention, by two pliable plastic sheets joined together by conventional means to form inflatable chambers within the calf straps (3, 4, 5). Filling the calf straps (3, 4, 5) with air moves the welded joints (7) of the two pliable plastic sheets that were joined together to form the air chambers within the calf straps (3, 4, 5) well away from a patient's skin of the calf over the tibia when the calf straps (3, 4, 5) are each independently snugged up against the skin of the calf over the tibia to secure the improved inflatable foot cushion (1) of the present invention about the CAF of the patient. The inflatable calf straps (3, 4, 5) are each connected at one end thereof to one downwardly-sloping side (16) of the main chamber (6) in fluid communication with the main chamber (6), and at the other end each calf strap (3, 4, 5) is adjustably attached to the opposite downwardly sloping side (17) of the main chamber (6) with hook and loop fasteners (13, 14). By this novel design of the secured inflated calf straps (3, 4, 5) of the improved inflatable foot cushion, the calf and ankle are fully supported and kept snug through 360 degrees by equalized static air pressures (cf., Boyles Law and Paschal Principles). Not only do the air-filled calf straps (3, 4, 5) deliver non-gradient air pressure to the calf, but as mentioned above, they also keep the sealed construction edges (7) of the air-filled straps (3, 4, 5) away from the skin of the calf over the tibia. Neither of these novel design features was present in the Inflatable Foot Cushion of U.S. Pat. No. 5,328,445.

Figure 1:
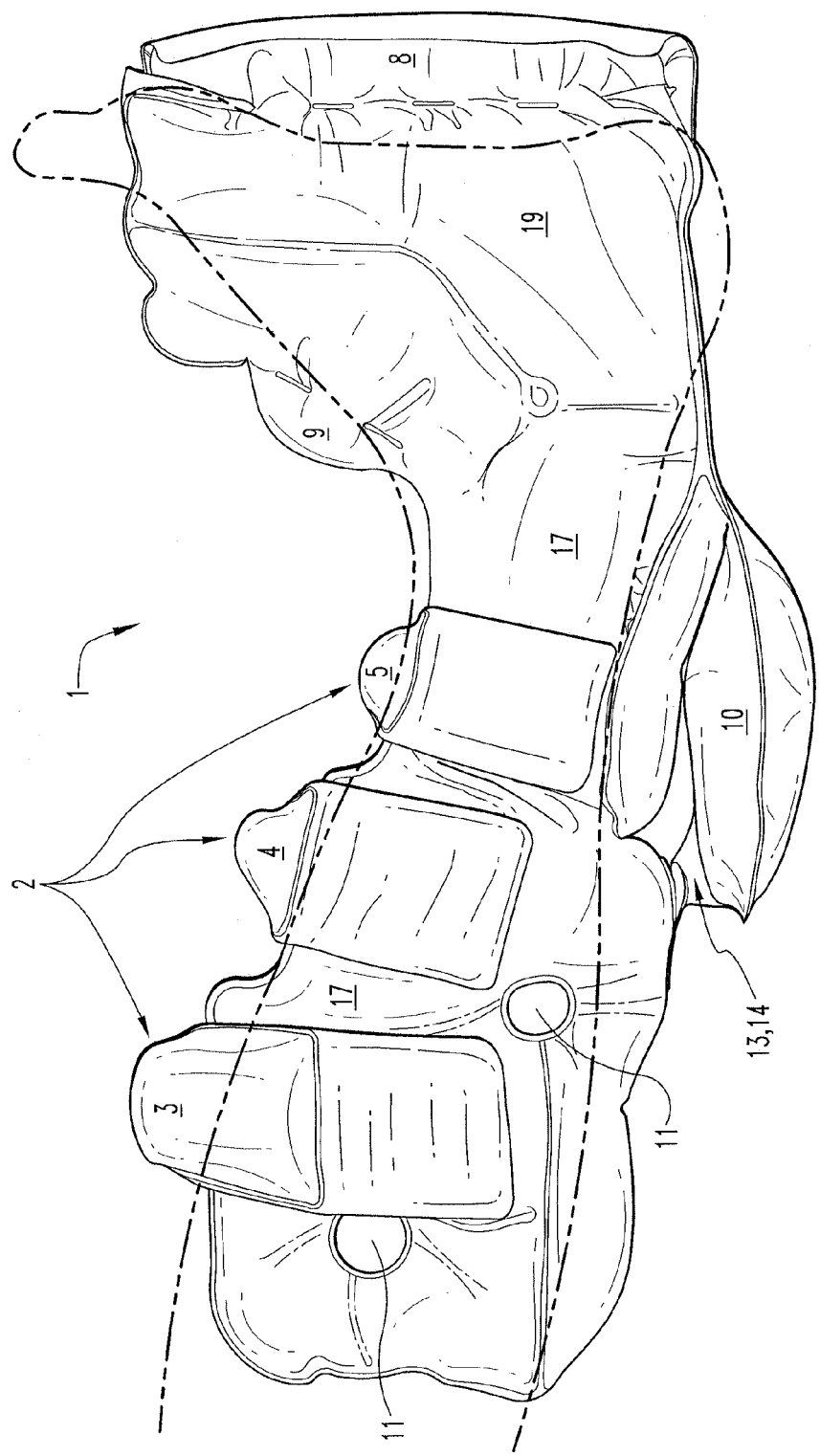
FIG. 1 is a right side elevation view of the novel inflatable foot cushion of the present invention.

The second novel improvement of the inflatable foot cushion (1) of the present invention is the sloped-downward design of the sides (16, 17) of the main chamber (6), which slope downwardly from the calf to the ankle areas of the main chamber (6) (see FIG. 1). The use of the air filled calf straps (3, 4, 5) allows this lower side profile of the sides (16, 17) of the main chamber (6) to be used effectively to provide for better ambient air circulation around the calf and ankle area, which in combination with through holes (11) in the sides (16, 17) provides for better ambient air control (both temperature and moisture control) around the calf and ankle. The novel inflatable foot cushion (1) of the present invention (1) thus permits more ambient air to enter the novel inflatable cushion and surround the calf and ankle areas. To improve ambient air circulation calf strap (5) may be freed from its securing hook and loop fasteners (13, 14) on side (17) of the main chamber (6) and temporarily the hook faster (14) of calf strap (5) may be attached to loop fastener (20) shown on side (17) (FIG. 2) of main chamber (6).

In testing done to date, the lower side profile of the downwardly-sloping sides (16, 17) of the main chamber (6) also reduces the chance for lateral rotation of the CAF within the main chamber (6), and reduces the chances for an over extension or flexion of the patient's knee and a lateral rotation of the patient's hip. This is a major improvement over the Inflatable Foot Cushion of U.S. Pat. No. 5,328,445, as that device is balloon-like in its overall structure, and it therefore has a tendency to roll from side-to-side when either over or under inflated with air. The lower profile, downwardly sloping sides (16, 17) of the present invention also allow patients wearing the novel inflatable foot cushion (1) to articulate their ankles and to move their foot fore and aft while it is snuggly embraced within the novel inflatable foot cushion (1) of the present invention.

The third and fourth novel improvements of the inflatable foot cushion (1) of the present invention, discussed below, relate to the prevention of the inflatable foot cushion (1) of the present invention from spinning on its longitudinal axis, which compromises the desired CAF positioning within the device, and which occurs at times when the Inflatable Foot Cushion of U.S. Pat. No. 5,328,445 is in use.

The third novel improvement of the inflatable foot cushion (1) of the present invention is a novel air filled and adjustable foot strap (9) that is connected in fluid communication with the foot chamber cushion (19) of main chamber (6), and it passes from foot chamber cushion (19) to foot chamber cushion (18) where it is adjustably attached to foot cushion chamber (18) of the main chamber (6) with hook and loop fasteners (13, 14). In this manner, the air filled and adjustable foot strap (9) covers the skin on top of a foot positioned within the main chamber (6) which prevents the CAF from inadvertently slipping out of the novel inflatable foot cushion (1) of the present invention in use. The foot strap (9) also allows for a complete customizable fitting of a patient's within the novel inflatable foot cushion (1) of the present invention. This novel feature can be compared to the lacing or strapping of normal footwear to the foot.

Figure 6:
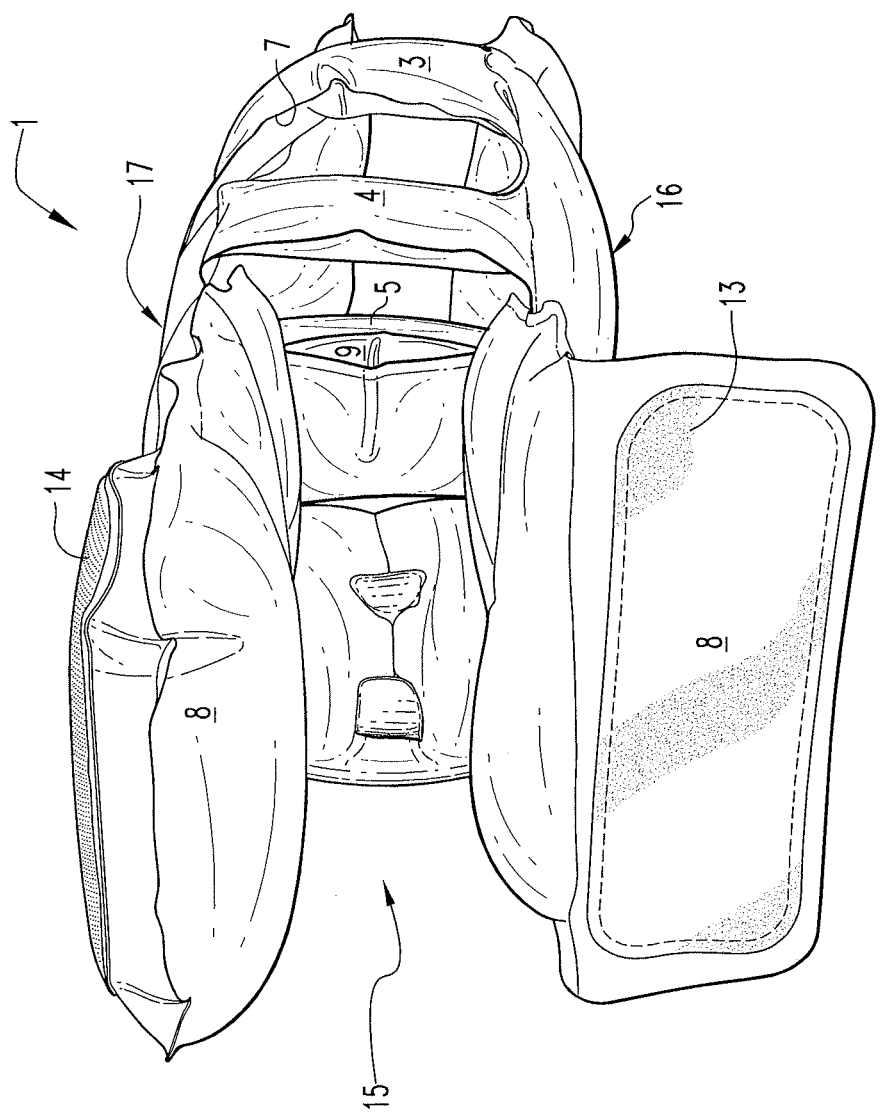
FIG. 6 is a front perspective view of the novel inflatable foot cushion of the present invention.
Figure 7:
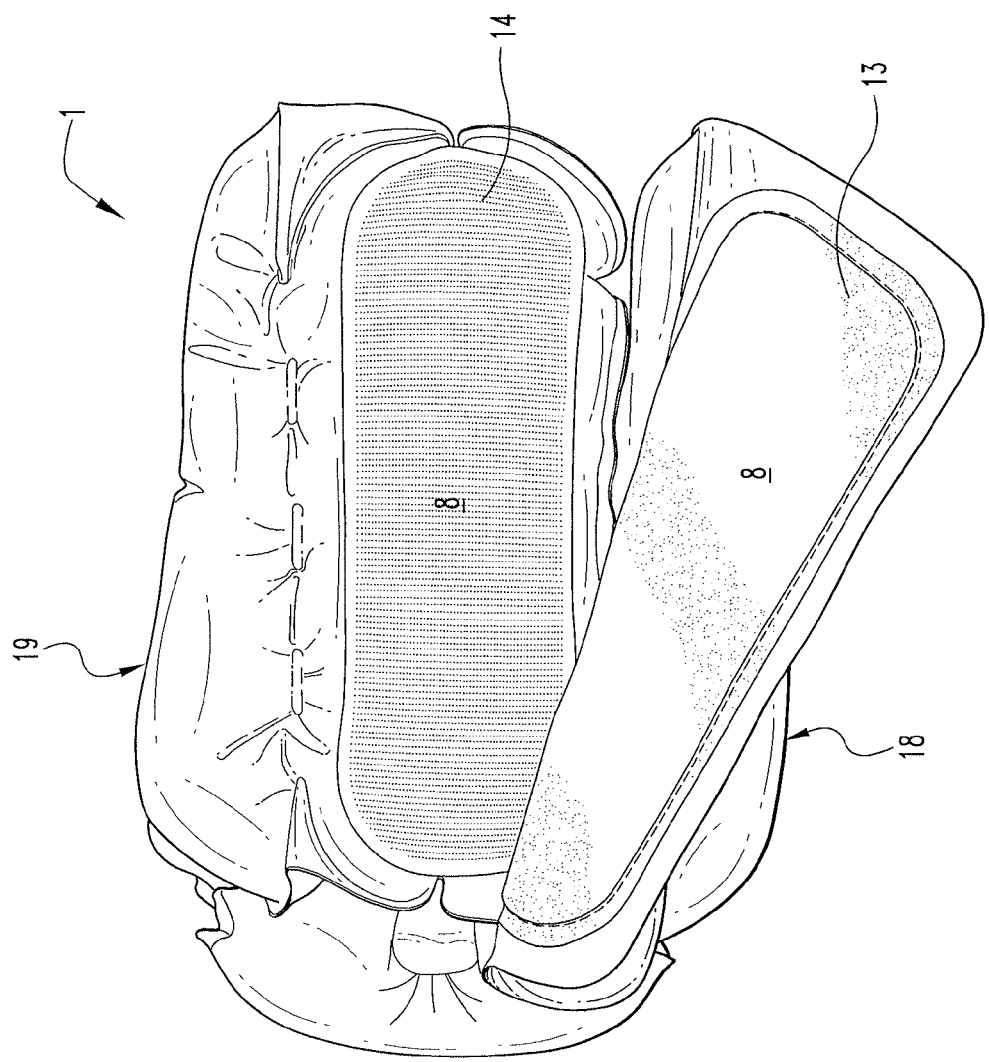
FIG. 7 is a front end view of the novel inflatable foot cushion of the present invention.

The fourth novel improvement of the inflatable foot cushion of the present invention (1) is the novel design of the adjustable, inflatable foot sole cushion (8) that is adjustable in two parts (see FIGS. 6 & 7) with hook and loop fasteners (13, 14) to match the contours of the sole of a foot within the novel inflatable foot cushion (1) of the present invention. The adjustable and inflatable two-part foot sole cushion (8) has one part thereof in fluid communication with foot chamber cushion (18) and the other part in fluid communication with foot chamber cushion (19), and foot sole cushion (8) thereby allows a more custom fit of the inflatable foot cushion (1) of the present invention to the sole of a patient's foot. It is adjustable with large hook and loop fasteners (13, 14) (FIGS. 6 & 7) which also protects the sides of a foot from being too tightly fit within the novel inflatable cushion (1) of the present invention. The uniform shape of the foot sole cushion (14) of the Inflatable Foot Cushion of U.S. Pat. No. 5,328,445 was not able to accomplish this custom fit to the sole of a foot.

Figure 3:
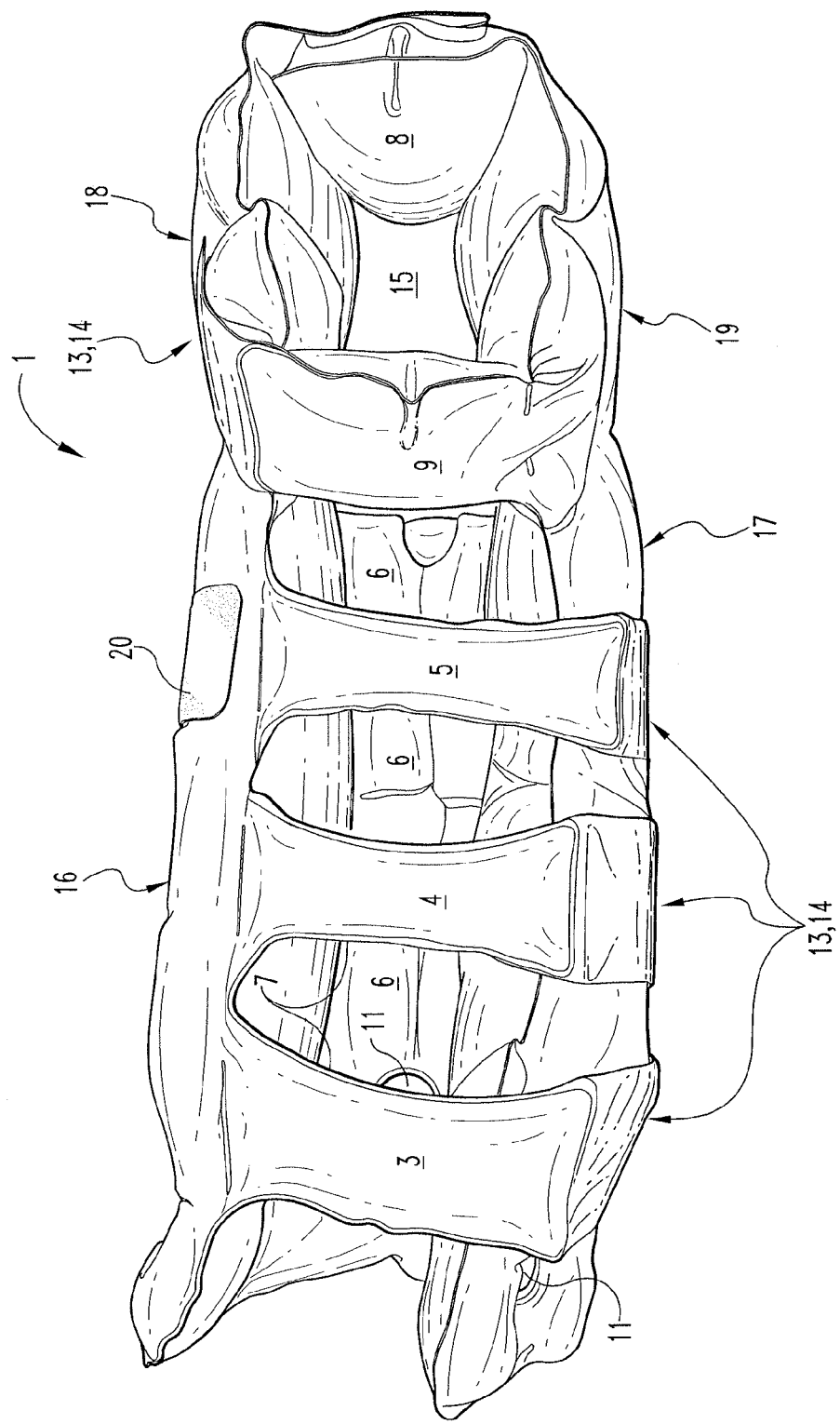
FIG. 3 is a top plan view of the novel inflatable foot cushion of the present invention.
Figure 4:
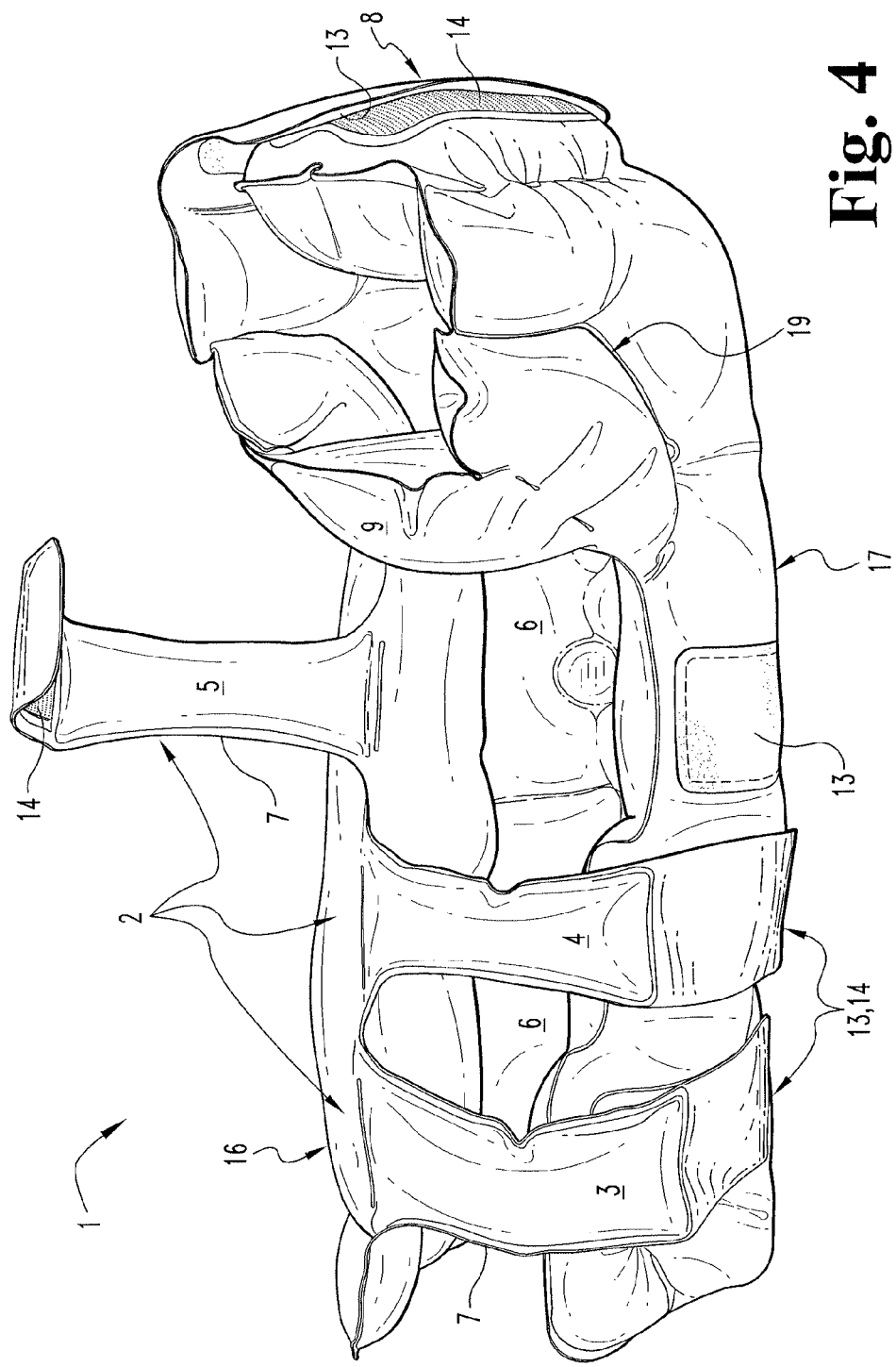
FIG. 4 as a right side perspective view of the novel inflatable foot cushion of the present invention.
Figure 5:
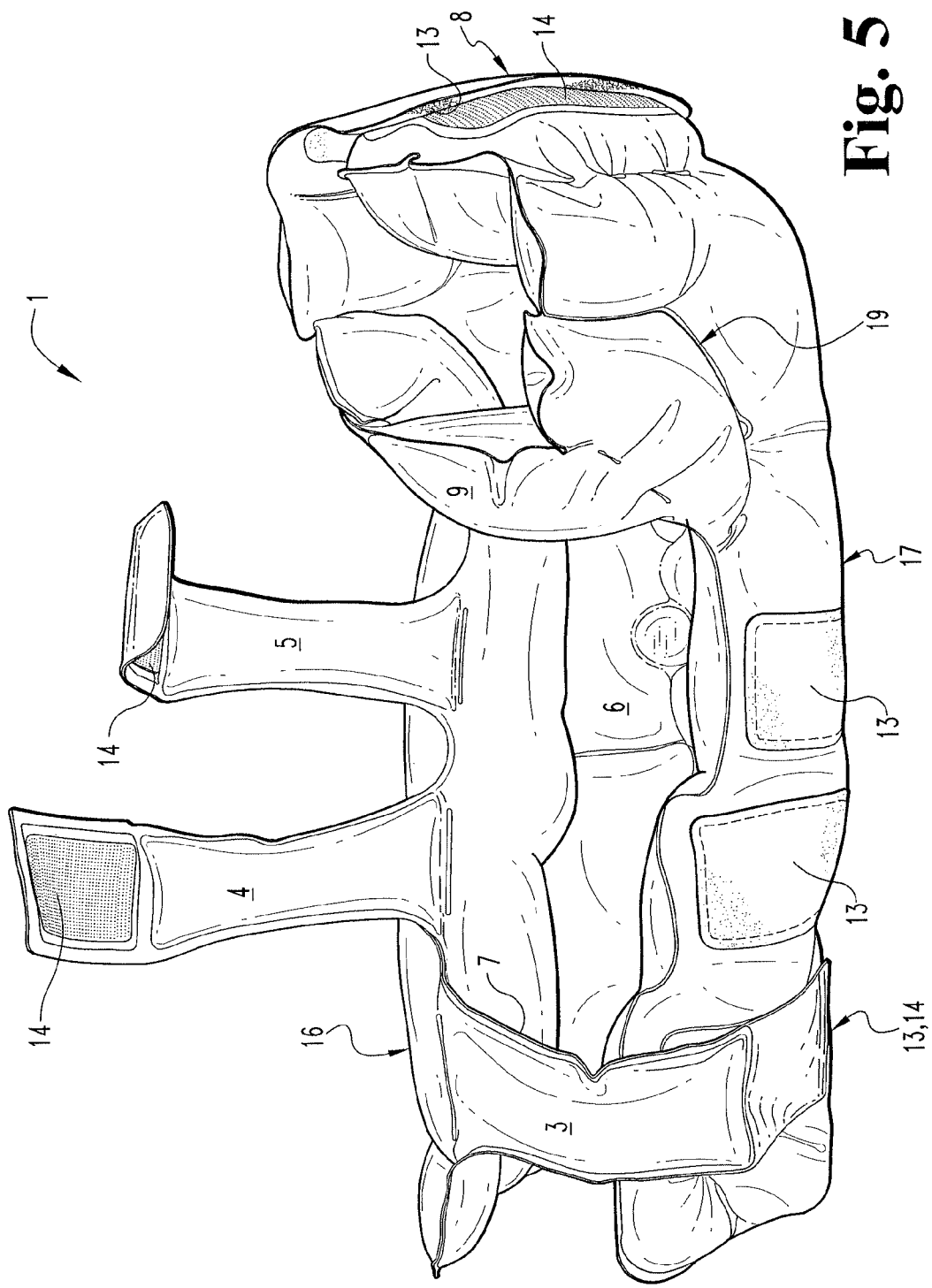
FIG. 5 is a right side perspective view of the novel inflatable foot cushion of the present invention.

The adjustable, inflatable two-part foot sole cushion (8) also creates a desirably larger hole (15) in main chamber (6) for a patient's heel to reside within, unsupported (see FIGS. 1, 3 & 6), than was created in the Inflatable Foot Cushion of U.S. Pat. No. 5,328,445. This fact, coupled with the functionality of foot strap (9) and foot sole cushion (8), which keep a foot up, thereby preventing "foot drop" (see FIG. 1), also effectively protects the entire Achilles heel area, as well.

Furthermore, when the two-part foot sole cushion (8) is opened completely by disassociating the adjustable hook and loop fasteners completely (13, 14) (see FIG. 7), the patient's foot sole is fully exposed, and the patient could then become ambulatory, moving from a bed to a chair, for example, while still wearing the novel inflatable foot cushion (1) of the present invention, which was not a possibility with the Inflatable Foot Cushion of U.S. Pat. No. 5,328,445.

In testing to date, the third and fourth novel improvements of the present invention also assisted in preventing the spinning of the inflatable foot cushion (1) of the present invention on its longitudinal axis, which occurred at times when the Inflatable Foot Cushion of U.S. Pat. No. 5,328,445 is over or under inflated.

In summary, these foregoing novel improvements present within the inflatable foot cushion (1) of the present invention address the maintenance of proper anatomical positioning of the CAF when it is in use; they deliver a low profiled static air support through in 360 degrees to the CAF so that skin and soft tissue distortion, ischemia, lymphatic and interstitial fluid obstruction and reperfusion injuries are less likely to occur, when the novel inflatable foot cushion (1) of the present invention is in use.

The following two tables summarize in tabular format the differences between the novel inflatable foot cushion (1) of the present invention ("2011 Device") and the Inflatable Foot Cushion of U.S. Pat. No. 5,328,445 ("1994 Device").

TABLE I

|  | 1994 Device | 2011 Device |
|---|---|---|
| Delivers Static Air Support to the Calf/Ankle/Foot ("CAF") | Yes | Yes |
| Offloads the Heel | Yes | Yes |
| Protects Achilles Tendon | Yes | Yes |
| Has Air Filled, Adjustable Strapping | No | Yes |
| Protects the Medial Malleolus | Yes | Yes |

TABLE II

Rating of Effectiveness 1-5
(5 = Excellent-1 = Poor)

|  | 1994 Device | 2011 Device |
|---|---|---|
| Unloads the Heel | 5 | 5 |
| Delivers Non-Gradient Static Air Support | 5 | 5 |
| Addresses Microclimate (Heat, Moisture) | 4 | 5 |
| Prevents Foot Drop | 3 | 4 |
| Prevents Lateral Rotation | 3 | 4 |
| Prevents Over-Extension of the Knee | 4 | 5 |
| Safety of the Adjustable Straps | 4 | 5 |
| Foot Compartment Customizing Ability | 2 | 5 |
| Prevention of the CAF Spinning, and Improper Positioning | 3 | 5 |
| Ease of Use | 4 | 5 |
| Cost Effective | 5 | 5 |

We claim:

1. A two-sided air-inflatable foot cushion configured to reduce force amplifications upon the heel of a foot received therein when a body is in a supine position, comprising:

an air-inflatable, adjustable foot strap connected in fluid communication at a first end thereof to either a first side or a second side of the two-sided air-inflatable foot cushion and removably and adjustably affixed at a second end thereof to the other of the first side or the second side of the two-sided air-inflatable foot cushion that when inflated is adapted to overlay at least a portion of a skin on a top of a foot when the foot is positioned within the two-sided air-inflatable foot cushion; and an air-inflatable sole cushion having a first part and a second part, the first part being adjacent to, and in fluid communication with, at least the first side of the two-sided air-inflatable foot cushion, the second part being adjacent to, and in fluid communication with, at least the second side of the two-sided air-inflatable foot cushion, the first part having an upper surface and a lower surface, the upper and lower surfaces being on opposing sides of the first part, the air-inflatable sole cushion displaceable between an open position and a closed position, the upper surface of the first part positioned to extend across a bottom segment of the foot, and the lower surface overlays, and is adjustably secured to, an upper surface of the second part when the air-inflatable sole cushion is in the closed position, the first and second parts being detached from each other to expose a bottom segment of the foot when the air-inflatable sole cushion is in the open position.

2. The two-sided air-inflatable foot cushion of claim 1, wherein air-inflatable, adjustable foot strap is adapted to extend from a first foot cushion chamber of the two-sided air-inflatable foot cushion, a second end of the air-inflatable, adjustable foot strap being adapted to be removably and adjustably affixed to a second foot cushion chamber of the two-sided air-inflatable foot cushion, the first and second foot cushion chambers adapted to be positioned at least along opposing sides of the foot when the foot is positioned in the two-sided air-inflatable foot cushion.

3. The two-sided air-inflatable foot cushion of claim 2, wherein a first part of the air-inflatable sole cushion extends from one of the first foot cushion chamber and the second foot cushion chamber, and a second part of the air-inflatable sole cushion extends from the other of the first foot cushion chamber and the second foot cushion chamber.

4. The two-sided air-inflatable foot cushion of claim 3, wherein the air-inflatable sole cushion includes a hole positioned to receive passage of a portion of a heel of the foot that is positioned within the two-sided air-inflatable foot cushion when the air-inflatable sole cushion is in a closed position.

5. The two-sided air-inflatable foot cushion of claim 4, wherein an air-inflatable, adjustable foot strap is adapted to remain affixed to the second foot cushion chamber when the air-inflatable sole cushion is in an open position.

6. The two-sided air-inflatable foot cushion of claim 5, wherein the entirety of a sole of the foot that is positioned within the two-sided air-inflatable foot cushion is fully exposed when the air-inflatable sole cushion is in the open position.

7. The two-sided air-inflatable foot cushion of claim 6, wherein the first foot cushion chamber extends from, and is in fluid communication with, a first downwardly sloping side of the two-sided air-inflatable foot cushion, and the second foot cushion chamber extends from, and is in fluid communication with, a second downwardly sloping side of the two-sided air-inflatable foot cushion, the first and second downwardly sloping sides sloping from a calf to ankle areas of the two-sided air-inflatable foot cushion.

8. The two-sided air-inflatable foot cushion of claim 7, further including a plurality of air-inflatable calf straps, each of the plurality of air-inflatable calf straps separated from an adjacent one of the plurality of air-inflatable calf straps to provide a passageway for a flow of ambient air, the plurality of air-inflatable calf straps extending from, and being in fluid communication with, one of the first downwardly sloping side and the second downwardly sloping side and selectively attachable to the other of the first downwardly sloping side and the second downwardly sloping side.

9. A two-sided air-inflatable foot cushion configured to reduce force amplifications upon a heel of a foot received therein when a body is in a supine position, the two-sided air-inflatable foot cushion comprising:
an air-inflatable, adjustable two-sided foot sole cushion having a first side and a second side that are in fluid communication with the inflatable foot cushion, the first side adapted to overlay the second side beneath a bottom segment of the foot when the first side is positioned to be removably and adjustably affixed to the second side, whereby the two-sided foot sole cushion is adapted to adjust to a contour of a sole of a foot that is positioned within the inflatable foot cushion, the first and second sides further adapted to be selectively separated from each other to expose the bottom segment of the foot.

10. The two-sided air-inflatable foot cushion of claim 9, wherein the air-inflatable, adjustable two-sided foot sole cushion includes a hole positioned to receive passage of a portion of a heel of the foot that is positioned within the air-inflatable, adjustable two-sided foot sole cushion and a first side overlaps a second side beneath a bottom segment of the foot.

11. The two-sided air-inflatable foot cushion of claim 10, further including an air-inflatable, adjustable foot strap adapted to extend across an upper region of the foot and remain affixed to a portion of the air-inflatable, adjustable two-sided foot sole cushion when the first and second sides are selectively separated from each other.

12. The two-sided air-inflatable foot cushion of claim 11, wherein an entirety of a sole of the foot that is positioned within the two-sided air-inflatable foot cushion is fully exposed when the first and second sides are selectively separated from each other.

13. The two-sided air-inflatable foot cushion of claim 12, wherein the air-inflatable, adjustable two-sided foot sole cushion extends from, and is in fluid communication with, a first downwardly sloping side and a second downwardly sloping side of the two-sided air-inflatable foot cushion, the first and second downwardly sloping sides sloping from a calf to ankle areas of the inflatable main chamber.

14. The two-sided air-inflatable foot cushion of claim 13, further including a plurality of air-inflatable calf straps, each of the plurality of air-inflatable calf straps being separated from an adjacent one of the plurality of air-inflatable calf straps to provide a passageway for a flow of ambient air, the plurality of air-inflatable calf straps extending from, and being in fluid communication with, one of the first downwardly sloping side and the second downwardly sloping side and selectively attachable to the other of the first downwardly sloping side and the second downwardly sloping side.

15. The two-sided air-inflatable foot cushion of claim 9, further comprising:
an inflatable main chamber having two inflatable downwardly-sloping sides downwardly sloping from a calf to an ankle area of the inflatable main chamber to improve ambient air circulation, each side of the inflatable main chamber being connected in fluid communication with an adjacent one of the two inflatable downwardly-sloping sides, which are adapted to support with static air pressures the calf, ankle and foot of a body in a supine position, leaving the heel of the foot free of support by the inflatable main chamber, when the calf, ankle and foot are positioned within the two-sided air-inflatable foot cushion;
a plurality of inflatable, adjustable calf straps connected in fluid communication at a first end thereof with one of the two inflatable downwardly-sloping sides and removably and adjustably affixed at a second end thereof to the other of the two inflatable downwardly-sloping sides, which are adapted to overlay at least a portion of a skin on a calf along a tibia when a calf is positioned within the two-sided air-inflatable foot cushion; and
an inflatable, adjustable foot strap connected in fluid communication at one end thereof with one side of the inflatable main chamber and removably and adjustably affixed at the other end thereof to the other side of the inflatable main chamber that is adapted to overlay at least a portion of the skin on a top of a foot when the foot is positioned within the two-sided air-inflatable foot cushion.

16. The two-sided air-inflatable foot cushion of claim 9, further comprising:
an inflatable main chamber having, when positioned about a calf and ankle areas and when the body is in a supine position, two inflatable downwardly-sloping sides downwardly sloping from the calf to the ankle areas of the inflatable main chamber to improve ambient air circulation with each side of the inflatable main chamber being connected in fluid communication with an adjacent one of the two inflatable downwardly-sloping side, which are adapted to support with static air pressures the calf, ankle and foot of a body in a supine position, leaving the heel of the foot free of support by the inflatable main chamber, when the calf, ankle and foot are positioned within the two-sided air-inflatable foot cushion, and further structured to facilitate articulation of the foot when the calf, ankle and foot are positioned within the two-sided air-inflatable foot cushion.

17. The two-sided air inflatable foot cushion of claim 9, further comprising:
a plurality of air-inflatable, adjustable calf straps connected in fluid communication at one end thereof to one side of the two-sided air inflatable foot cushion, the plurality of air-inflatable, adjustable calf straps adapted for inflation to equalized static air pressures to deliver non-gradient pressure to a calf, the plurality of air-inflatable, adjustable calf straps being further adapted to overlay a portion of a skin on a calf when the calf, ankle and foot are positioned within the two-sided air inflatable foot cushion.

* * * * *